United States Patent [19]

Dubeck et al.

[11] 4,107,104

[45] Aug. 15, 1978

[54] HALOGENATED XYLENES

[75] Inventors: Michael Dubeck, Birmingham; David R. Brackenridge, Royal Oak, both of Mich.

[73] Assignee: Ethyl Corporation, Richmond, Va.

[21] Appl. No.: 363,789

[22] Filed: May 25, 1973

Related U.S. Application Data

[63] Continuation-in-part of Ser. No. 70,922, Sep. 9, 1970, abandoned.

[51] Int. Cl.$^2$ .................. C08G 18/32; C08G 18/14
[52] U.S. Cl. ................................................. 521/171
[58] Field of Search ............... 260/2.5 AM, 2.5 AJ, 260/618 D

[56] References Cited

U.S. PATENT DOCUMENTS

| | | | |
|---|---|---|---|
| 2,028,715 | 1/1936 | Hanson | 252/8.1 |
| 2,631,168 | 3/1953 | Ross | 260/618 |
| 3,259,593 | 7/1966 | Eichhorn | 260/2.5 AJ |
| 3,422,047 | 1/1969 | Cannelongo | 260/28.5 |
| 3,660,321 | 5/1972 | Praetzel | 260/2.5 AJ |
| 3,738,953 | 6/1973 | Anorga | 260/2.5 AJ |

OTHER PUBLICATIONS

Journal of Amer. Chem. Soc., vol. 68, 1946, pp. 424–425.

*Primary Examiner*—C. Warren Ivy
*Attorney, Agent, or Firm*—Donald L. Johnson; John F. Sieberth; James M. Pelton

[57] ABSTRACT

Compounds having the formula

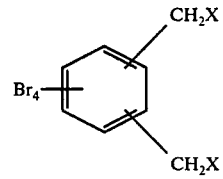

where X is a halogen, ester, hydroxyl, alkoxy, amine, cyanide, or isocyanate radicals. These compounds are useful as flame retardant additives for polymers, especially for polyurethane foams.

8 Claims, No Drawings

HALOGENATED XYLENES

CROSS REFERENCE TO RELATED APPLICATION

This application is a continuation-in-part of co-pending application Ser. No. 70,922, filed Sep. 9, 1970, now abandoned.

BACKGROUND OF THE INVENTION

Certain halogenated aromatic compounds are known in the art. For example, polychlorinated benzene and xylene compounds are disclosed in U.S. Pat. Nos. 2,564,214 and 2,631,168. Typical substituents on the methyl groups of the xylene are chlorine, hydroxyl, methoxy, ethoxy, propoxy, carboxyl, acetate, isocyanate, chloroformate, thiol, and amine radicals. The compounds are stated to be useful as monomers for condensation reactions producing self-extinguishing resins, as heat transfer media, as modifiers for increasing the flash point of oils, in transformer fluids, lubricating media, and the like.

SUMMARY OF THE INVENTION

This invention relates to novel flame retardant polyurethane foam compositions comprising a reaction product of a polyisocyanate and a polymer selected from the class consisting of hydroxyl-terminated polyethers and hydroxyl-terminated polyesters having incorporated therein a flame retardant amount of a tetrabrominated xylene compound. In the polyurethane foam composition the tetrabrominated xylene compound can have the general formula

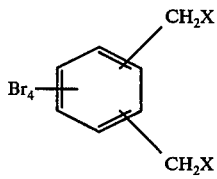

wherein X is selected from hydrogen, bromine and hydroxyl groups. Several of the foregoing tetrabrominated xylene compounds are novel compounds per se.

DESCRIPTION OF THE PREFERRED EMBODIMENTS

The novel compounds disclosed by the general formula above are derivatives of tetrabrominated xylene in which the methyl groups are substituted with various preferred radicals. This invention contemplates the novel compounds to include all the tetrabrominated xylene compounds; for example, the tetrabrominated o-, m- and p-xylenes.

A preferred group of derivatives of the halogenated compounds are those described by the general formula above wherein X is a radical selected from the group consisting of bromide, hydroxyl and acetate radicals. Of course, these derivatives include the o-, m- and p-isomers of the tetrabrominated xylenes.

A preferred substituent radical is a halogen radical. A most preferred halogen is bromide. Thus, the halogen can be the same as or different than that substituted on the aromatic nucleus of the xylene ring. Typical compounds in which the halogen is bromine are selected from the group consisting of α,α'-2,3,5,6-hexabromo-p-xylene, α,α'-2,4,5,6-hexabromo-o-xylene, and α,α'-2,4,5,6-hexabromo-m-xylene.

Another preferred substituent radical is the hydroxyl radical. Typical compounds in which the hydroxyl radical is substituted on the methyl groups of a tetrabrominated xylene compound are selected from the group consisting of 2,3,5,6-tetrabromo-p-xylene-α,α'-diol, 3,4,5,6-tetrabromo-o-xylene-α,α'-diol, and 2,4,5,6-tetrabromo-m-xylene-αα'-diol.

Another preferred substituent radical is an ester radical. By the term "ester radical" is meant an organic acid in which the hydrogen is removed from the hydroxyl group, leaving a highly reactive species having the general formula

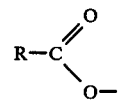

where R represents a hydrocarbon radical. The ester radicals may be selected from radicals having from 1 to about 20 carbon atoms. A preferred group of ester radicals contains from 1 to about 12 carbon atoms. A most preferred range of carbon atoms on the ester radicals is from 1 to 4 carbon atoms. Thus, typical ester radicals are formate, acetate, propionate, butyrate, hexanoate, heptanoate, octanoate, decanoate, laurate, tridecanoate, hexadecanoate, octadecanoate, eicosanoate, and the like. Among the compounds which may be prepared using the above radicals, a preferred group are prepared from the acetate radical. Thus, preferred compounds prepared using the acetate radical are selected from 2,3,5,6-tetrabromo-p-xylene-α,α'-diol diacetate, 3,4,5,6-tetrabromo-o-xylene-α,α'-diol diacetate, and 2,4,5,6-tetrabromo-m-xylene-α,α'-diol diacetate.

Another preferred radical is the alkoxy radical. Alkoxy radicals having from 1 to about 20 carbon atoms are useful for preparing novel compounds of this invention. Preferred alkoxy radicals from have 1 to about 12 carbon atoms, with the most preferred alkoxy radicals ranging from 1 to 4 carbon atoms. The compounds prepared using the alkoxy radicals are typically 2,3,5,6-tetrabromo-α,α'-dimethoxy-p-xylene,
3,4,5,6-tetrabromo-α,α'-diethoxy-o-xylene,
2,4,5,6-tetrabromo-α,α'-dipropoxy-m-xylene,
2,3,5,6-tetrabromo-α,α'-dibutoxy-p-xylene,
3,4,5,6-tetrabromo-α,α'-dipentoxy-o-xylene,
2,4,5,6-tetrabromo-α,α'-dioctoxy-m-xylene,
2,3,5,6-tetrabromo-α,α'-didecaoxy-p-xylene,
3,4,5,6-tetrabromo-α,α'-didodecaoxy-o-xylene,
2,4,5,6-tetrabromo-α,α'-dibutodecaoxy-m-xylene,
2,3,5,6-tetrabromo-α,α'-dihexadecaoxy-p-xylene,
3,4,5,6-tetrabromp-α,α'-diheptadecaoxy-o-xylene,
2,4,5,6-tetrabromo-α,α'-dinonadecaoxy-m-xylene,
2,3,5,6-tetrabromo-α,α'-dieicosaoxy-p-xylene.

Another preferred embodiment of the substituent radicals is an amine radical. Ammonia and the organic amines can be used as substituents on the methyl groups of tetrabrominated xylenes. Thus, organic amines having from 1 to about 20 carbon atoms are useful as substituent radicals. A preferred group of organic amines are those having from 1 to about 12 carbon atoms. Most preferred organic amines are those having from 1 to 4 carbon atoms.

The novel compounds of this invention can be prepared by brominating xylene and subsequently reacting the tetrabrominated xylene thereby producing by a free radical mechanism to substitute the methyl side chains. Tetrabromo-p-xylene can be prepared according to known methods by reacting a xylene with bromine in the presence of a Friedel-Crafts catalyst at about 0° C. Preparation of tetrabromo-p-xylene is illustrative of the preparation of various isomers and is illustrated in the following example. In this and other examples, all parts are by weight unless otherwise stated.

EXAMPLE I

In a glass resin flask, a mixture of 1000 parts bromine and 3 parts of aluminum tribromide was cooled at 5° C and 83 parts of p-xylene were added dropwise with rapid stirring and continued cooling. After adding about 3/4 of the xylene, the reaction mixture became viscous forming large chunks of product. The mixture was diluted with 454 parts of bromine and the temperature was brought to 30° C. The heating and stirring gradually broke down the chunks of product to a fine powder. The mixture was then cooled to 15° C and the remaining xylene was added. Most of the excess bromine was removed by distillation. The solid was removed from the reaction flask and leached with cold methanol to remove excess bromine. The product was then dissolved in hot benzene and filtered. The solvent was then driven off and 323 parts (98.3% yield) of tetrabromo-p-xylene was obtained as crystals having the melting point of 253°–254° C.

The reaction procedure for preparation of the tetrabrominated-o- and m-xylenes is similar with the exception of using o- or m-xylene to replace p-xylene in the above example.

Tetrabromoxylene can then be brominated to prepare the compounds of this invention by reaction with additional bromine in the presence of a solvent and a source of irradiation for the production of free radicals. The preparation of $\alpha,\alpha'$-2,3,5,6-hexabromo-p-xylene is typical for the preparation of the brominated derivatives of this invention. Such preparation is illustrated in the following example.

EXAMPLE II

To a reaction flask equipped with a stirrer was added 42 parts of tetrabromo-p-xylene. This was then dissolved by adding 80 parts of carbon tetrachloride and the reaction flask was flushed with nitrogen. A nitrogen blanket was then maintained in the reaction flask. To this mixture was added 32 parts of bromine in carbon tetrachloride over a period of two hours while the reaction mixture was refluxing. A 150-watt light was positioned to shine into the flask during reaction. After rapid uptake of the bromine during the addition of the first one-half of the bromine, the solution became milky and a white solid began to precipitate. The refluxing was continued overnight and then the reaction mass was cooled to 0° to 5° C and the mixture was filtered and the crystals produced were washed with cold carbon tetrachloride. After drying, 55 parts of a white powder having melting points of 272.5° to 273.5° C were produced. The total yield of $\alpha,\alpha'$-2,3,5,6-hexabromo-p-xylene was 58 parts or about 99.5 percent. Analysis showed the following results: Percent bromine calculated — 82.8; found — 82.2.

The preparation of $\alpha,\alpha'$-3,4,5,6-hexabromo-o-xylene and $\alpha,\alpha'$-2,4,5,6-hexabromo-m-xylene is similar to Example II except tetrabromo-o- and m-xylenes, respectively, are used.

The tetrabrominated xylene diol diacetate is prepared by reacting the $\alpha,\alpha'$-dibromo derivative of tetrabromoxylene with a sodium salt of the ester to be substituted in the presence of a carboxylic acid reaction media. The preparation of 2,3,5,6-tetrabromo-p-xylene-$\alpha,\alpha'$-diol diacetate is illustrative.

EXAMPLE III

A mixture of $\alpha,\alpha'$-2,3,5,6-hexabromo-p-xylene, 25 parts, sodium acetate, 25 parts, and acetic acid, 420 parts, was heated in a reaction vessel to reflux with stirring. After heating and stirring for about one hour, the mixture appeared as a clear solution and then became cloudy after 2 hours. The mixture was then cooled and the acetic acid stripped from the reaction mixture. The resulting solid was triturated with water and the white residue resulting therefrom was filtered and air dried to yield 22.3 parts of 2,3,5,6-tetrabromo-p-xylene-$\alpha,\alpha'$-diol diacetate, melting at 232°–234° C. This represents a yield of about 96 percent.

Similar results are obtained when the $\alpha,\alpha'$-2,3,5,6-hexabromo-p-xylene is replaced by the similar ortho- and metahexabrominated xylene derivatives.

The diol derivatives can be prepared by reacting the tetrabromoxylene diol diacetate derivatives with water in the presence of an alkali metal hydroxide and an ether according to known procedures. The 2,3,5,6-tetrabromo-p-xylene-$\alpha,\alpha'$-diol is illustrative of the preparation of the diol derivative.

EXAMPLE IV

A solution of potassium hydroxide, 20 parts, in water, 50 parts, was added dropwise to a refluxing solution of 20 parts 2,3,5,6-tetrabromo-p-xylene-$\alpha,\alpha'$-diol diacetate, prepared as in Example III above, in p-dioxane, 200 parts. After 2 hours at reflux the mixture was cooled somewhat and the bulk of the dioxane-water removed by a rotary evaporator. Water was added to the semi-solid residue, the precipitate filtered, washed with water and air dried to give crude diol, 16.7 parts. Recrystalization from dioxane-water gave 12.2 parts 2,3,5,6-tetrabromo-p-xylene-$\alpha,\alpha'$-diol, melting at 262°–263.5° C. A second crop, 3.95 parts, melted at 260–262° C. A third crop, 0.4 parts, melted at 225°–245° C. Combining the first two crops gives a yield of 96 percent. Analysis showed the following results: Percent bromine calculated — 70.5; found — 71.5.

Following the procedures outlined in the preceding examples, various other preferred tetrabrominated xylene derivatives can be produced according to this invention. In general, the alkoxy derivative of tetrabrominated xylenes can be prepared by reacting $\alpha,\alpha'$-2,3,4,5-hexabromo-o-xylene, for example, with an alkali metal alkoxide of the desired carbon chain length or the alkali metal hydroxide and the desired alcohol in water. For example, the preparation of 2,3,4,5-tetrabromo-$\alpha,\alpha'$-diethoxy-o-xylene can be made by reacting $\alpha,\alpha'$-2,3,4,5-hexabromo-o-xylene with aqueous sodium hydroxide in excess ethanol under reflux conditions. Further illustrating the preparation of the alkoxy derivative of various tetrabrominated xylene isomers, the following alcohols can be used: ethanol, propanol, butanol, pentanol, octanol, decanol, dodecanol, tetradecyl alcohol, cetyl alcohol, carnaubyl alcohol, ceryl alcohol, melissyl alcohol, tarchonyl alcohol and the like.

Other preferred tetrabrominated xylenes are the amine derivatives. For example, 2,3,5,6-tetrabromo-p-xylene-$\alpha,\alpha'$-diamine can be prepared by reacting $\alpha,\alpha'$-

2,3,5,6-hexabromo-p-xylene with ammonia in the presence of an excess of lutidine solvent. Similarly the ortho and meta isomers of the hexabrominated xylene may be used and the ammonia can be replaced with various organic amines having from 1 to about 20 carbon atoms. In addition, various forms of amines can be employed such as liquid ammonia or sodamide. Likewise, the various solvents may be used so long as the reactants are at least slightly soluble in the solvent and the solvent is substantially inert under the reaction conditions. Preferably, the organic amine may have from 1 to about 4 carbon atoms, such as methyl amine, ethyl amine, propyl amine, butyl amine and their various isomers. The primary amine is preferred.

Another preferred embodiment of the tetrabrominated xylene derivatives of this invention is the preparation of the cyanide derivative from the hexabrominated xylenes. Generally, the cyanide derivative is prepared by replacing the bromine on the methyl groups of the hexabrominated xylene with a suitable source of cyanide ions such as potassium cyanide, sodium cyanide, hydrogen cyanide and the like, in the solvent such as dimethylformamide, tetrahydrofuran and the like. Illustrative of this process is the preparation of 2,3,5,6-tetrabromo-p-xylene-α,α'-dinitrile. This compound can be made by reacting α,α'-2,3,5,6-tetrabromo-p-xylene dissolved in excess dimethylformamide with potassium cyanide. Of course, the hexabrominated ortho- and meta-xylene isomers may also be used in the starting material to produce the corresponding dinitrile. The dinitrile derivatives can be hydrogenated according to well known techniques to produce a diamine derivative. This is a further alternative to the production of the tetrabrominated xylene diamines described hereinabove. A further alternative within the scope of this invention is the hydrolysis of the dinitril with base such as alkali or alkaline earth metal hydroxide to produce the alkali or alkaline earth metal salts of carboxylic acid having one more carbon atom than the methyl group originally found on xylene.

Another preferred embodiment of this invention is the isocyanate derivative of tetrabrominated xylene. In general, the isocyanate derivative can be prepared by reacting the hexabromoxylene with an alkali metal isocyanate, preferably sodium or potassium isocyanate, in a suitable solvent. Suitable solvents for the preparation of tetrabrominated xylene isocyanates are dipolar solvents, such as, tetrahydrofuran or dimethylformamide. As an illustration of the preparation of these isocyanate derivatives, 2,3,5,6-tetrabromo-p-xylene-α,α'-diisocyanate can be produced by reacting α,α'-2,3,5,6-hexabromo-p-xylene in an excess of dimethylformamide as a solvent with potassium isocyanate. Of course the ortho- and meta-xylene derivatives may be used to produce corresponding diisocyanate derivatives.

It should be understood by one skilled in the art that having prepared the novel hexabrominated xylene compounds, the bromine atoms attached to the methyl groups may be replaced by other functional groups according to known procedures of classical organic chemistry. Thus, the nitro, aldehyde, keto, thiol, sulfate, phosphate and like derivatives may be prepared, for example, from α,α'-2,3,5,6-hexabromo-p-xylene.

The novel compounds of this invention are useful as chemical intermediates, monomers for condensation resins, and additive or reactive-type flame retardants.

For example, the α,α'-3,4,5,6-hexabromo-o-xylene may be hydrolyzed with water to form the diol and then oxidized to form tetrabromophthalic acid. This compounds is a well-known flame retardant for polyester resins.

The novel compounds of this invention may also form reaction products with a wide variety of complementary functional groups. For example, among the types of reactants with which the novel compounds of this invention may be condensed are alcohols, mercaptans and amines. As examples of the polyfunctional reactants with which reactions are possible, there may be mentioned ethylene glycol, propylene glycol, butylene glycol, diethylene glycol, triethylene glycol, dipropylene glycol, dimethanol dimethyl methane, 2-mercapto methanol, dihydroxy ethyl sulfide, glycerol, trimethanol ethyl methane, d-sorbitol, d-sorbose methanol, hydroxy ethyl cellulose, propylene dimercaptan and hexamethylene diamine.

In the instances where hydroxyl, diol and/or amino radicals constitute the functional groups in the novel compounds of this invention, they may be reacted with acids, acid anhydrides and acid chlorides; such as, succinic acid, sebacic and, adipic acid, pimelic acid, suberic acid, azelaic acid, undecanedioic acid, dodecanedioic acid, tetradecanedioic acid, octadecanedioic acid, agathic acid, phthalic acid, and terephthalic acid. The anhydrides such as maleic anhydride and phthalic anhydride and the chlorides of the foregoing acids may also be used.

In general, the tetrabrominated xylene derivatives of this invention can be used as additive-type flame retardants for polymers or resins of either the thermoplastic or thermosetting type. Standard methods for incorporating additives, such as stabilizers, plasticizers, fillers and the like, into polymers or resins can be employed to add the flame retardant materials of this invention. Typically, a flame retardant amount of the tetrabrominated xylene derivative is added. By flame retardant amount is meant an amount sufficient to decrease the flammability of the polymer or resin. Generally, from about 2 to about 40 weight percent of the tetrabrominated xylene derivative can be used. Preferably, from about 5 to about 25 weight percent is added to the polymer or resin. It should be recognized that greater or lesser amounts can be employed, taking into account the polymer or resin substrate and whether or not the flame retardant of this invention is used in conjunction with another flame retardant additive.

Further, the tetrabromoxylene diols and diacetate may be used as reactive-type flame retardants. Incorporation and reaction with other monomers, as described hereinbelow, requires substantially similar amounts as the additive-type materials.

In addition, another embodiment of this invention employs the starting material for the novel compounds of this invention, tetrabromoxylene, as an additive-type flame retardant for polymers and resins. Tetrabromoxylene can be employed at from about 2 to about 40 weight percent based on the polymer or resin into which it is incorporated. The method of incorporation is well within the skill of the art.

Accordingly, a preferred embodiment of this invention is a flame retardant polymer composition comprising a polymer or resin and a flame retardant amount of a compound having the formula

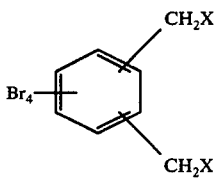

wherein X is selected from hydrogen, bromine, hydroxyl, and acetoxy groups.

Another preferred embodiment of this invention is a flame retardant composition comprising a polyester resin and a flame retarding amount of a compound having the formula

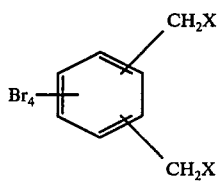

wherein X is selected from hydrogen, bromine, hydroxyl, and acetoxy groups. The novel flame retardant compositions of this invention can be prepared by incorporating the above brominated xylene compounds into a polyester produced by reacting a polyhydric alcohol and a dicarboxylic acid or its anhydride. Typically, an aliphatic unsaturated dicarboxylic acid or anhydride, such as maleic acid or maleic anhydride, or an aromatic dicarboxylic acid or anhydride, such as phthalic acid or phthalic anhydride, or mixtures of these, are used. Polyhydric alcohols, such as ethylene glycol, propylene glycol, neopentyl glycol, and the like, are typical of those preferred.

The brominated xylene compounds are preferably used in amounts corresponding to a polyester containing from 10 to 40 percent by weight of the brominated xylene compound and sufficient to provide a total of from about 5 to 25 percent by weight of bromine in the product.

The polyester composition can be prepared by reacting a dicarboxylic acid and a polyhydric alcohol according to methods known in the art, see Kirk-Othmer, *Encyclopedia of Chemical Technology*, Vol. 16, pp. 143–189, Interscience Publishers, New York, N. Y., and the references there included. In addition to the flame retardant compounds of this invention, the polyester can also include stabilizers, chain terminators, colors improvers, delustrants and the like.

The novel compounds of this invention can be added to the polyester. However, the tetrabrominated xylene diols, which are polyhydric alcohols, can be incorporated into the polymer chain as a reactive species. Accordingly, 2,3,5,6-tetrabromo-p-xylene-α,α'-diol, for example, ethylene glycol, maleic anhydride and phthalic anhydride can be reacted at reflux temperature to produce a resin product. The resin can be cooled and styrenated and polymerized with t-butyl-hydroperoxide to produce a self-extinguishing polymer. Similarly, self-extinguishing polymers can be prepared using the diacetoxy derivative of tetrabrominated xylene.

When carrying out the preparation of flame retarded polyesters with the tetrabrominated or hexabrominated xylenes, the material is not incorporated into the polyester chain but is in contrast an additive-type flame retardant. Thus, the polyester resin may be prepared beforehand and the flame retarding agent incorporated during polymerization or after polymerization by blending into the polymer using known procedures. Thus, the tetrabrominated or hexabrominated xylene may be added by milling with the resin, for example, on a two-roll mill, in a Banbury mixer, or by simultaneous molding, such as by extruding with the resin. Additionally, the tetrabrominated or hexabrominated xylene may be added during resin manufacture, e.g., during polymerization, provided the catalyst and other ingredients of the polymerization system are inert to the tetrabrominated or hexabrominated xylene or the polymerization conditions are not deleterious. The following example illustrates the incorporation of the novel compounds of this invention into a polyester resin as an additive-type flame retardant. All parts are by weight unless otherwise indicated.

EXAMPLE V

To 100 parts of polyester resin (General Purpose Resin Polylite 31-007 from Reichold Chemical) containing 57 weight percent with 42–43 weight percent syrene was added 12.08 parts of α,α'-2,3,5,6-hexabromo-p-xylene and 1 part of benzoyl peroxide curing agent. The polyester resin was cured between glass plates which were gasketed and clamped together. The mixture was allowed to gel overnight at 50° C in an oven. The glass plates, clamps and gasket were removed and the polyester sheet was post-cured at 80° C for 3 hours. Samples were cut from the sheet and tested according to ASTM-D-2863-70 for flammability.

Similar procedures were followed for preparing flame retardant polyester sheet containing 13.08 parts of tetrabromo-m-xylene and tetrabromo-p-xylene and 12.08 parts of α,α'-2,4,5,6-hexabromo-m-xylene. The results of these tests are shown on the table below.

Similar results are obtained using the diol and diol diacetate derivatives of the tetrabrominated xylene compounds, but, of course, they are more preferably employed as reactive-type flame retardant additives according to the procedure as illustrated hereinabove. These flame retardant additives may likewise be incorporated into polyethylene, polypropylene, polystyrene, polybutylene, acrylonitrile-butadiene-styrene, and the like.

EXAMPLE VI

To 45 g of general purpose polypropylene resin (Profax-6523 from Hercules Powder) was added 5.44 g (12.08 weight percent) of α,α'-2,3,5,6-hexabromo-p-xylene and 0.9 (2 wt %) g of chopped fiber glass. The ingredients were mixed initially by hand and then for 3 minutes in a Waring Blender to assure substantially complete homogeneity. Then 45 g of this mixture was charged into a chase-type mold measuring 6 inches × 4 inches × ⅛ inch. The mixture was covered with mirror-finish aluminum foil and placed in a heated press. After 1½ minutes warm-up, the pressure was increased to 10,000 psig and held for 1½ minutes at 400° F. The assembly was then removed from the press and quenched in cold water. The molded sheet was cut into 10 long samples which were used to test the flammability of the flame retarded polypropylene in accordance with ASTM-D-2863-70. The results of this test are given in the table below.

Similar procedures are used to prepare flame retardent polypropylene containing 12.08 weight percent of α,α'-2,4,5,6-hexabromo-m-xylene and 13.08 weight percent of tetrabromo-p- and m-xylene.

As well as being a reactive-type flame retardant, the tetrabrominated xylene diol can also be added to polypropylene Similar results are obtain using the diol and diol diacetate derivatives of the tetrabrominated xylene compounds, but, of course, they are more preferably employed as reactivetype flame retardant additives according to the procedure as illustrated hereinabove.

Preferably, the novel compounds of this invention can be incorporated into polyurethane polymers which can be made according to known methods. The brominated xylene compounds can be simply added to the mixture to be foamed.

Polyrurethane foams are formed from compositions comprising
(i) a polymer containing free hydroxyl groups such as hydroxyl-terminated polyesters or hydroxylterminated polyethers,
(ii) a polyisocyanate, and
(iii) a foaming agent.

Usually, other materials are added to the composition to be foamed such as
(iv) catalysts,
(v) plasticizers, and
(vi) emulsifiers,
for example.

The polyesters may be derived from a reaction product of a dicarboxylic acid such as adipic acid, and a dihydric alcohol such as ethylene glycol, and may be modified by a material such as trimethylolpropane; confer pages 20–21 of Ferrigno, *Rigid Plastic Foams*, Reinhold Publishing Corp., New York, N.Y. (1963).

The polyethers are ethylene oxide and propylene oxide adducts of polyhydric alcohols and are described on pages 10–19 of Ferrigno, supra.

Polyisocyanates which can be used are described in U.S. Pat. No. 3,574,148, supra; confer the paragraph bridging columns 3 and 4. Another description of exemplary isocyanates is in U.S. Pat. No. 3,338,846, in the first two paragraphs of Column 8.

Foaming agents such as water and urethanes described from tertiary alcohols are known; confer U.S. Pat. No. 3,338,846. Fluorocarbon blowing agents are described in U.S. Pat. No. 3,574,149.

For the other ingredients which can be added to make rigid or flexible polyurethane foams, reference is also made to U.S. Pat. Nos. 3,338,845; 3,338,846; and 3,574,149; all cited above, and U.S. Pat. No. 3,409,580 which are all hereby incorporated by reference herein as if fully set forth.

In general, a fire retardant amount of the tetrabrominated xylene derivative can be employed in the polyurethane formulation. Typically, the amount used is based on one of the components, for example, the polyol. In general, from about 2 to about 40 parts by weight per each 100 parts by weight of polyol, and more preferably from about 5 to about 25 parts per 100 parts by weight polyol are used. It should be understood that greater or lesser quantities of the tetrabrominated xylene derivative can be employed as desired.

The exact nature of the polyurethane foam or the ingredients admixed to prepared the foam are not critical, since the fire retardance of the additives is not unduly restricted by the foams or the ingredients from which the foams are made.

The following procedure illustrates the preparation of polyurethane foam without the flame retardant additive of this invention.

EXAMPLE VI

To 100 grams of polyoxypropylene polyol (Pluracol GP-3030) having an average molecular weight of 2920 and a hydroxyl number of 56, were added 1.0 grams of silicone surfactant (Dow Corning 192), 0.3 grams tertiary amine blowing catalyst (DABCO 33-L), and 4.0 grams of distilled water. The dispersion was mixed thoroughly for 10 seconds. Then, 0.2 grams of stannous octoate catalyst was added and mixed for 5 seconds. Next, 50.0 grams of an 80:20 blend of the 2,4- and 2,6-isomers of toluene diisocyanate were added and stirred rapidly for 10 seconds or until creaming was noted. The resulting admixture was poured into a 8 × 8 × 4 box and allowed 3–5 minutes for the foaming reaction to take place. Then the foam was placed in an oven and cured for 30 minutes at about 120° C.

The foam was removed from the oven, aged for seven days at ambient temperature, and cut into test specimens for flammability testing.

Using the procedure of Example VI, several polyurethane foams were prepared incorporating the flame retardant additives of this invention. The flame retardant was added to the polyol with the surfactant, blowing catalyst and water. Then same procedure for foaming and curing was used. The following table gives the flame retardant additive, amount of flame retardant added and density of the final foam.

Flame Retardant Polyurethane Foams Prepared According to Example VI

| Example | Flame Retardant | Amount Added to Dispersion of Example VI | Density pfc |
|---|---|---|---|
| VII | 2,3,5,6-Tetrabromo-p-xylene-α,α'-diol | 10 | 1.85 |
| VIII | 2,3,5,6-Tetrachloro-p-xylene-α,α'-diol | 10 | 1.80 |
| IX | 2,4,5,6-Tetrabromo-m-xylene-α,α'-diol | 10 | — |
| X | 2,4,5,6-Tetrachloro-m-xylene-α,α'-diol | 10 | — |
| XI | 2,3,5,6-Tetrabromo-p-xylene-α,α'-dibromide | 10 | 1.7 |
| XII | 2,3,5,6-Tetrabromo-p-xylene-α,α'-dibromide | 15 | 1.9 |
| XIII | 2,3,5,6-Tetrachloro-p-xylene-α,α'dibromide | 10 | 1.85 |
| XIV | 2,3,5,6-Tetrachloro-p-xylene-α,α'-dichloride | 10 | 1.8 |
| XV | 2,4,5,6-Tetrabromo-m-xylene-α,α'-dibromide | 10 | 1.57 |
| XVI | 2,4,5,6-Tetrachloro-m-xylene-α,α'-dibromide | 10 | — |
| XVII | Tetrabromo-p-xylene | 10 | 1.7 |
| XVIII | Tetrabromo-p-xylene | 15 | 1.9 |

The foams produced in Examples VI-XVI were subjected to flammability testing in accordance with ASTM-D-2863-70, also known as the Limiting Oxygen Index and ASTM-D-1692-59T. The test results are shown below. Several chlorinated analogs of the flame retardant additives of this invention were also tested for comparison. Also, in several cases the flame retardant additives of this invention and their chlorinated analogs were incorporated as additive-type flame retardants in polyester, according to the procedure of Example V, for comparison.

| | Flammability Test Results | | | |
|---|---|---|---|---|
| | ASTM-D-1692-59T | ASTM-D-2862-70 | | |
| | Polyurethane | | Polyester | |
| Example | Burning Rate (in./min.) | Polyurethane LOI | Loading (Wt %) | LOI |
| Blank* | — | — | — | 18.4 |
| VI (Blank) | 7.0 | 16.7 | — | — |
| VII | 2.0 | 18.7 | 14.2 | 19.7 |
| VIII | 4.8 | 18.5 | 14.2 | 20.0 |
| IX | 1.9 | 18.9 | — | — |
| X | 4.5 | 18.1 | — | — |
| XI | 5.4 | 19.3 | 12.08 | 19.4 |
| XII | 5.5 | 19.3 | — | — |
| XIII | — | 20.2 | 12.08 | 20.6 |
| XIV | — | 18.9 | — | — |
| XV | 3.4 | 20.2 | — | — |
| XVI | 2.0 | 19.8 | — | — |
| XVII | 4.0 | 18.5 | 13.08 | 20.6 |
| XVIII | 3.15 | 18.97 | — | — |

*Prepared as in Example V, except no flame retardant used.

The above results show that the tetrabrominated xylene compounds of this invention provide effective flame retardance for polyurethane foam, as shown in comparing the blank (Example VI) with Examples VII, X, XI, XII, XV, XVII and XVIII. Further, the comparison of the tetrabrominated xylene diol compounds with their chlorinated analogs shows unexpectedly superior flame retardance for polyurethane, see for example the results of the burn rates and LOI values of Examples VII and IX, compared with Examples VIII and X, respectively. Such comparison is especially significant when considering that the results of the testing in polyester indicates that the chlorinated analogs have somewhat better LOI values.

Likewise, foams with improved flame retardancy can be made with the corresponding tetrabromo-o-xylene-α,α'-diols are used in an amount of from 5 to about 25 parts per 100 parts by weight of polyol. Similar results are obtained when the tetrabromo-p- and -m-xylene-α,α'-diols are used in an amount of from 5 to 25 parts per each 100 parts of hydroxy-containing polymer.

Similar results are obtained when the molecular weight of the hydroxy-terminated polymer has an average molecular weight of from about 1250 to about 2800.

Similar results are obtained when the above amounts of tetrabromo-xylene-diols are added to the compositions of Examples 1–5 of U.S. Pat. No. 3,338,846, and the compositions of Examples 1–24 of U.S. Pat. No. 3,338,845 and 3,409,580.

Similar results are obtained when the isocyanate is an 80/20 mixture of 2,4/2,6-tolylene diisocyanate or a p,p'-diphenylmethane diisocyanate or PAPI.

Similar results are obtained when the foaming agent is trichlorofluoromethane or dichlorodifluoromethane.

What is clamed is:

1. A polyurethane foam composition produced by reaction of an organic polyisocyanate, a foaming agent and a polymer selected from the class consisting of hydroxylterminated polyethers and hydroxyl-terminated polyesters and said polyurethane foam having incorporated therein a flame retardant amount of a tetrabrominated xylene-α,α'-diol compound having the formula

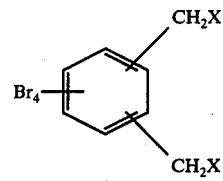

wherein x is a hydroxyl radical.

2. A composition of claim 1 wherein said polymer is a hydroxyl-terminated polyether.

3. The composition of claim 1 wherein said polymer is a hydroxyl-terminated polyether and said tetrabrominated xylene compound has the formula

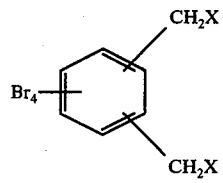

wherein X is a hydroxyl radical.

4. The composition of claim 1 wherein said tetrabrominated xylene compound is present at from about 2 to about 40 weight percent based on said polymer.

5. The composition of claim 1 wherein said tetrabrominated xylene compound is [selected from ] 2,3,5,6-tetrabromo-p-xylene-α.α'-diol [2,4,5,6-tetrabromo-m-xylene-α,α'-diol and 3,4,5,6-tetrabromo-o-xylene-α,α'-diol].

6. The composition of claim 1 wherein said polymer is a hydroxyl-terminated polyether and said tetrabrominated xylene compound is 2,3,5,6-tetrabromo-p-xylene-α,α'-diol which is present at about 2 to about 25 weight percent based upon said polyether.

7. The composition of claim 1 wherein said tetrabrominated xylene compound is 2,4,5,6-tetrabromo-m-xylene-α,α'-diol.

8. The composition of claim 1 wherein said said tetrabrominated xylene compound is 3,4,5,6-tetrabromo-o-xylene-α,α'-diol.

* * * * *

UNITED STATES PATENT OFFICE
CERTIFICATE OF CORRECTION

PATENT NO. : 4,107,104
DATED : August 15, 1978
INVENTOR(S) : Michael Dubeck and David R. Brackenridge It is certified that error appears in the above-identified patent and that said Letters Patent are hereby corrected as shown below:

Column 8, line 1, "durinc" should read -- during --. Column 8, line 22, "syrene" should read -- styrene --. Column 12, line 41, "[selected from]" should be deleted. Column 12, lines 42, 43 and 44, "[2,4,5,6-tetrabromo-m-xylene-$\alpha,\alpha'$-diol and 3,4,5,6-tetrabromo-o-xylene-$\alpha,\alpha'$-diol]" should be deleted. Column 12, line 53, "said said" should read -- said --.

Signed and Sealed this

Nineteenth Day of June 1979

[SEAL]

Attest:

RUTH C. MASON
Attesting Officer

DONALD W. BANNER
Commissioner of Patents and Trademarks